(12) United States Patent
Giordano et al.

(10) Patent No.: US 8,519,144 B2
(45) Date of Patent: Aug. 27, 2013

(54) PROCESS FOR THE PREPARATION OF ARYL-PIRIDYL COMPOUNDS

(75) Inventors: Claudio Giordano, Milan (IT); Luca Giannini, Pavia (IT)

(73) Assignee: Euticals Prime European Therapeuticals SpA, Lodi (IT)

( * ) Notice: Subject to any disclaimer, the term of this patent is extended or adjusted under 35 U.S.C. 154(b) by 1929 days.

(21) Appl. No.: 10/530,080

(22) PCT Filed: Oct. 2, 2002

(86) PCT No.: PCT/IT02/06625
§ 371 (c)(1),
(2), (4) Date: Jul. 16, 2006

(87) PCT Pub. No.: WO2004/037790
PCT Pub. Date: May 6, 2004

(65) Prior Publication Data
US 2006/0264640 A1     Nov. 23, 2006

(51) Int. Cl.
*C07D 213/48*     (2006.01)
(52) U.S. Cl.
USPC .......................................... 546/339; 546/340
(58) Field of Classification Search
None
See application file for complete search history.

(56) References Cited

U.S. PATENT DOCUMENTS 6,248,892 B1     6/2001   Noerenberg et al.

FOREIGN PATENT DOCUMENTS

| EP | 0 972 765 | 1/2000 |
|---|---|---|
| WO | WO97/40029 | 10/1997 |
| WO | WO01/27083 | 4/2001 |

OTHER PUBLICATIONS

Lohse, et al., "The Palladium Catalysed Suzuki Coupling of 2- and 4-Chloropyridines", *Synlett*, 1999, vol. 1, pp. 45-48.
Negishi, E., et al., "A Regiospecific Synthesis of Carbosubstituted Heteroaromatic Derivatives via Pd-Catalyzed Cross Coupling", Heterocycles, 1982, vol. 18, pp. 117-122.
Kalinin, V., "Carbon-Carbon Bond Formation in Heterocycles Using Ni- and Pd-Catalyzed Reactions", *Synthesis* 1992, 413-432.
Stanforth, S., "Catalyst Cross-Coupling Reactions in Biaryl Synthesis", *Tetrahedron*, 1998, 54, No. 3-4, pp. 263-303.
Tamao, K., et al., "Nickel-Phosphine Complex-Catalyzed Grignard Coupling—II", *Tetrahedron* vol. 38, No. 22, pp. 3347-3354, 1982.
Bold, G., et al., "New Aza-Dipeptide Analogues as Potent and Orally Absorbed HIV-1 Protease Inhibitors: Candidates for Clinical Development", *J. Med. Chem.*, 1998, 41, pp. 3387-3401.
Rabasseda, X., et al., "N'[2(S)-Hydroxy-3(S)-[N-(methoxycarbonyl)-1-tert-leucylamino]-4-phenylbutyl]-N$^\alpha$-(methoxycarbonyl)-N$^1$-[4-(2-pyridyl)benzyl]1-tert-leucylhydrazide", Drugs of the Future, 1999, 24(4):375.
Van Hecke et al., "Ditertiary Phosphine Complexes of nickel. Spetral, Magnetic, and Proton Resonance Studies. A Planar-Tetrahedral Equilibrium" *Inorg. Chem.*, 1966, 1968.
Trecourt, F., et al., "New Syntheses of Substituted Pyridines via Bromine-Magnesium Exchange", *Tetrahedron* 56 (2000), 1349-1360.
Pearson, D.E. et al., "A Study of the Entrainment Method for Making Grignard Reagents", JOC 1959, 24, 504.
Fischer et al., "Pyridineboronic Acids", *Recl. Trav. Chim. Pays Bas* 1965 (84), 439.

*Primary Examiner* — Zinna Northington Davis
(74) *Attorney, Agent, or Firm* — Fredrikson & Byron, P.A.

(57) ABSTRACT

A method is described for the preparation of aryl-pyridine compounds of formula (I) by cross-coupling reaction, promoted by catalytic systems based on palladium or nickel between compounds of formula (II) and (III) in which: -Met represents Mg or Zn, —Y represents Cl, Br, I or acetoxy, —Z represents I, Br, Cl, triflate, sulphonate, phosphate, —$R_1$, $R_2$, $R_3$, $R_4$, which are the same as one another or different, represent hydrogen, a linear and/or branched $C_1$-$C_4$ alkyl, and/or an aryl, and/or a heteroaryl, or $R_1$ and $R_2$ and/or $R_3$ and $R_4$, taken together, form a $C_3$-$C_8$ ring, an aryl and/or a heteroaryl, -A represents —$COR_5$ where $R_5$ represents hydrogen, a linear and/or branched $C_1$-$C_4$ alkyl, and/or an aryl, and/or a heteroaryl, or -A represents —$CR_{s5}(OR_6)(OR_7)$ where $R_5$ has the meaning described above and $R_6$ and $R_7$, which are the same as one another or different, represent a linear and/or branched $C_1$-$C_4$ alkyl, and/or an aryl, and/or a heteroaryl, or $R_6$ and $R_7$, joined together, represent a $C_1$-$C_8$ alkyl or alkenyl.

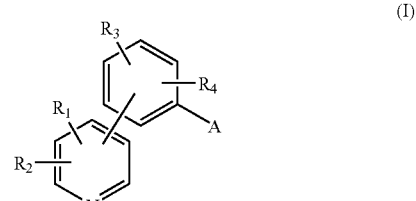

(I)

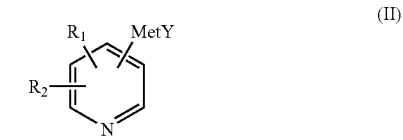

(II)

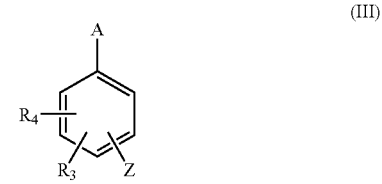

(III)

33 Claims, No Drawings

PROCESS FOR THE PREPARATION OF ARYL-PIRIDYL COMPOUNDS

RELATED APPLICATIONS

This application is a U.S. 371 national stage entry of International Application No. PCT/IT2002/006625, filed Oct. 2, 2002, the teachings of which are incorporated herein by reference.

The subject of the present invention is the preparation of compounds of formula 1:

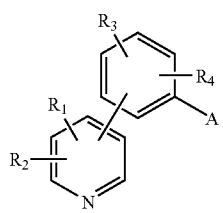

from compounds of formula 2 and formula 3.

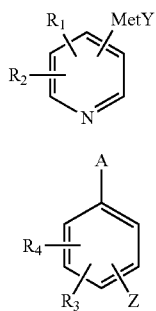

in which:
Met represents Mg or Zn,
Y represents Cl, Br, I or acetoxy,
Z represents I, Br, Cl, triflate, sulphonate, phosphate,
$R_1$, $R_2$, $R_3$, $R_4$, which are the same as one another or different, represent hydrogen, a linear and/or branched $C_1$-$C_4$ alkyl, and/or an aryl, and/or a heteroaryl or $R_1$ and $R_2$ and/or $R_3$ and $R_4$ taken together, form a $C_3$-$C_8$ ring, an aryl and/or a heteroaryl,
A represents —$COR_5$, where $R_5$ represents hydrogen, a linear and/or branched $C_1$-$C_4$ alky and/or an aryl, and/or a heteroaryl, or
A represents —$CR_5(OR_6)(OR_7)$ where $R_5$ has the meaning described above and $R_6$ and $R_7$, which are the same as one another or different, represent a linear and/or branched $C_1$-$C_4$ alkyl and/or an aryl, and/or a heteroaryl, or $R_6$ and $R_7$, joined together, represent a $C_1$-$C_8$ alkyl or alkenyl.

STATE OF THE ART

Aryl pyridines are commonly used in organic synthesis as intermediates for the preparation of compounds of various types.

4-(2'-pyridyl)benzaldehyde is an intermediate useful for the preparation of antiviral drugs and, in particular, of drugs effective in the treatment of AIDS, such as, for example, the heterocyclic azahexane derivatives described in International patent application WO 97/40029, which is incorporated herein by reference; amongst the antiviral drugs in question, for example, BMS-232632 Drugs of the Future 1999, 24(4): 375) are noteworthy.

Aryl pyridines can be prepared by aryl-aryl cross-coupling reactions (Lohse et al.: Synlett, 1999, Vol. 1; 45-48; Ei-ichi Negishi et al. Heterocycles 1982, Vol. 18 117-122). Generally, the pyridine derivative carries the leaving group and the aryl derivative is the metallo-organic reagent.

There is a limited number of examples of aryl-aryl cross-coupling in which the pyridine constitutes the organometallic reagent (Kalinin, D. N., *Synthesis* 1992, 413-432; *Tetrahedron* 1998, 54, 263-303).

Moreover, in the known examples of this type, the pyridine is hardly ever present in Grignard form, but is present as a boron derivative. An example in which it is shown that a pyridine Grignard does not give an effective cross-coupling reaction is reported in the literature (Kumada, M. et al *Tetrahedron* 1982, 38, 3347-3354). In particular, 4-(2'-pyridyl) benzaldehyde is normally prepared from 4 bromobenzaldehyde and 2-bromopyridine (Bold et al.; *J. Med. Chem.* 1998, 41, 3387 and Drugs of the Future, 1999, 24(4):375). The method provides for the conversion of the bromobenzaldehyde into the corresponding acetal and then into the Grignard reagent $BrMgC_6H_4CH(OR)_2$; the Grignard reagent is then reacted with 2-bromopyridine in the presence of $NiCl_2$ and of 1,3-bis(diphenylphosphino)propane (*Inorg. Chem.* 1966, 1968) to give 4-(2'-pyridyl)-benzaldehyde as a result of the conversion of the acetal function into aldehyde by treatment in an acid aqueous medium. However, this method has the great disadvantage of poor repeatability, which is worse, the smaller the quantity of catalyst used.

Patent application EP 0,972,765, on the other hand, claims a method for the synthesis of aryl-pyridine based on the use of catalysts based on ferrocenyl phosphines and palladium, starting with halogeno-pyridine and aryl Grignards. International patent application WO 01/27083 describes the preparation of aryl-pyridine compounds in which a pyridyl halide is reacted with an aryl-magnesium halide in the presence of a catalytic quantity of a zinc salt and of a catalytic quantity of palladium.

The aim of the work which led to the present invention was to find a novel and reliable aryl-aryl cross-coupling method capable of leading to the formation of aryl pyridine from pyridine Grignards or from pyridyl-zinc derivatives, with reproducible and industrially satisfactory yields even in the presence of very small quantities of catalyst, eliminating or at least minimizing the risk of competitive reactions resulting from the presence of alkyl halides in the reaction medium.

DESCRIPTION OF THE INVENTION

It has now surprisingly been found that compounds of formula 1 can be produced with high yields and purity by cross-coupling reaction between compounds of formula 2 and compounds of formula 3, promoted by catalytic systems based on palladium or nickel, in accordance with the scheme given below.

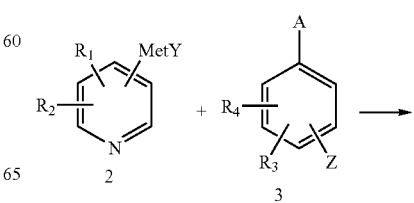

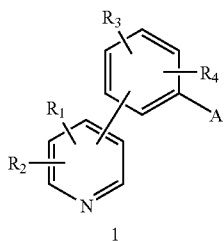

in which:
Met represents Mg or Zn,
Y represents Cl, Br, I or acetoxy,
Z represents I, Br, Cl, triflate, sulphonate, phosphate,
$R_1$, $R_2$, $R_3$, $R_4$, which are the same as one another or different, represent hydrogen, a linear and/or branched $C_1$-$C_4$ alkyl, and/or an aryl and/or a heteroaryl or $R_1$ and $R_2$ and/or $R_3$ and $R_4$, taken together, form a $C_3$-$C_8$ ring, an aryl and/or a heteroaryl,
A represents —$COR_5$, where $R_5$ represents hydrogen, a linear and/or branched $C_1$-$C_4$ alkyl and/or an aryl, and/or a heteroaryl or
A represents —$COR_5(OR_6)(OR_7)$ where $R_5$ has the meaning described above and $R_6$ and $R_7$, which are the same as one another or different, represent a linear and/or branched $C_1$-$C_4$ alkyl and/or an aryl and/or a heteroaryl or $R_6$ and $R_7$, joined together, represent a $C_1$-$C_8$ alkyl or alkenyl (for example, if a carbonyl function is protected as cyclic ketal).

Palladium and nickel are normally used in quantities of 0.01-10 moles, preferably 0.05-2 moles, per 100 moles of compound 2; the reaction is carried out by adding an organic solution of compound 2 to an organic solution containing compound 3 and the catalytic system.

The organic solvent is preferably an ethereal solvent (such as, for example, not to react with the Grignard compounds) such as THF, 1,2 dimethoxyethane, and/or 1,1-diethoxymethane or a mixture of solvents such as THF/toluene; the reaction is carried out at a temperature of between 20 and 100° C., preferably between 40 and 80° C.

The reaction yield can be increased by operating in the presence of phosphines and/or phosphites, to be used preferably in a molar ratio of catalyst-phosphine/phosphite of between 1:1 and 1:6. The phosphines usable for the purposes of the present invention may be: triaryl phosphines, such as triphenyl phosphine, tritolyl phosphine, trixylyl phosphine, tri-2-furyl phosphine; diyl alkylphosphines, such as methyldiphenyl phosphine, benzyldiphenyl phosphine, cyclohexyldiphenyl phosphine; dialkylaryl phosphines, such as 2-(di-t-butylphosphino)-biphenyl 2-(dicyclohexylphosphino) biphenyl; trialkyl phosphines, such as triisopropyl phosphine, tricyclohexyl phosphine, tributyl phosphine, triisobutyl phosphine, di-t-butylmethyl phosphine; bidentate phosphines such as 2-2'bis(diphenylphosphino)-1,1'binaphthyl (racemic BINAP), 1,2-bis(dicyclohexylphosphino)ethane, 1,1'bis (diphenyl-phosphino)ferrocene (dppf, 1,2-bis(diethylphosphino)-ethane, 1,2-bis(dipentafluorophenylphosphino) ethane, 1,3-bis(diphenylphosphino)propane (dppp), 1,4-bis (diphenyl-phosphino)butane (dppb). Palladium is generally added to the reaction medium in the form of complexes with phosphines such as, for example, palladium tetrakistriphenyl phosphine (Pd(PPh$_3$)$_4$) or as palladium salt, generally acetate or chloride, and a phosphine, preferably triphenyl phosphine; normally, one mole of palladium acetate or chloride is used in combination with 4 moles of triphenyl phosphine (Pd(OAc)$_2$ or PdCl$_2$+4PPh$_3$). Similarly, nickel is normally used in the form of complexes with phosphines, preferably bidentate phosphines, such as, for example, 1,3-bis(diphenylphosphino)propane (dppp) or 1,4-bis(diphenylphosphino)butane (dppb); these complexes are added to the reaction solution as salts such as, for example, Ni(dppp)Cl$_2$ or Ni(dppb)Cl$_2$.

Optionally, the reaction may also be carried out in the presence of zinc salts such as, for example, zinc chloride (ZnCl$_2$), zinc bromide (ZnBr$_2$) and zinc acetate (Zn(OAc)$_2$); the zinc salt is normally used in quantities of 25-120 moles, preferably 35-70 moles, per 100 moles of compound 2. In order for the cross-coupling reaction to proceed with high yields and high selectivity in the presence of a minimum quantity of catalyst, it is preferable to prevent the accumulation of Grignard reagents in the reaction medium and they should therefore be in a dynamic deficiency relative to the zinc salt (that is, the Grignard reagent is added dropwise to a solution already containing compound 3, palladium, phosphine binder, and zinc salt).

According to a preferred embodiment of the invention, 0.01-0.1 moles of palladium and 40-70 moles of zinc are used per 100 moles of compound 2; the molar ratio between palladium and compound 2 is less than 1:100. Alternatively, in a second embodiment, 0.01-2 moles of nickel per 100 moles of compound 2 are used (that is, in the absence of zinc salts).

The reaction according to the present invention may also be carried out both in the presence of alkyl halides (up to quantities greater than that which is equimolar with the Grignard), and in the presence of variable quantities of alkyl Grignard. This aspect is very important from an applicational point of view, since the preparations of pyridyl Grignards known in the literature (*Tetrahedron* 2000, 56, 1349 or in *JOC* 1959, 24, 504 and *Recl. Trav. Chim. Pays Bas* 1965, 84, 439) lead to solutions containing alkyl halides or alkyl-magnesium halides in variable quantities. It is therefore possible to use the organic solutions of the pyridyl Grignard selected, without further purification.

According to the preferred embodiment of the present invention, the compound of formula 2 is produced by reaction of the corresponding halogeno(bromo, iodo)-pyridine with a catalytic quantity of alkyl halide in the presence of an at least stoichiometric quantity of magnesium; the alkyl halide is normally a $C_1$-$C_8$ alkyl chloride or bromide, preferably ethyl bromide or isopropyl bromide or chloride. Preferably, 100 moles of halogeno-pyridine are reacted with 10-20 moles of alkyl halide and 100-120 moles of magnesium. The reaction is generally carried out at a temperature of 0-60° C., preferably at 15-35° C., in an aprotic organic solvent which does not react with a Grignard reagent, preferably in tetrahydrofuran or mixtures of tetrahydrofuran and toluene; the solution thus obtained is then added dropwise to the solution containing compound 3 and the catalytic system.

These and further aspects of the invention will become clear from the following examples which should be considered as illustrative and not limiting thereof.

Preparation of the Grignard Reagent

Example 1

Grignard A

Ethyl bromide (2.2 g 0.02 moles) was added to a suspension of magnesium (0.29 g, 0.12 moles) in anhydrous tetrahydrofuran (58.5 g) kept at 20° C., with stirring, in an inert atmosphere, whilst the internal temperature was kept below 35° C. 3-bromopyridine (16.0 g, 0.101 moles) was added over 3 hours to the solution thus obtained, whilst the temperature was controlled at between 25 and 30° C. Stirring of the reaction mixture was continued at 25° C. for a further 3 hours.

Example 2

Grignard B

A solution of 2-bromopyridine (16 g, 0.101 moles) in anhydrous tetrahydrofuran (5 g) was added over 1 hour to a solution of 2-propyl-magnesium chloride (2M in tetrahydrofuran, 50.6 ml, Aldrich cat. 2000/2001) kept at 25° C. Stirring of the mixture was continued at 2° C. for 4 hours.

Example 3

Grignard C

A solution of 2-propyl-magnesium chloride (2M in tetrahydrofuran, 51 g, 50.6 ml, Aldrich cat 2000/2001) was added over 1 hour to a solution of 2-bromopyridine (16 g, 0.101 moles) in anhydrous tetrahydrofuran (13 g), kept at 25° C. Stirring of the mixture was continued at 25° C. for 4 hours.

Example 4

Grignard D

A solution of 2-propyl-magnesium chloride (2M in tetrahydrofuran, 9.8 g 0.02 moles, Aldrich cat. 2000/2001) was added to a suspension of magnesium (1.96 g, 0.08 moles) in anhydrous tetrahydrofuran (53.2 g), kept at 20° C., with stirring, in an inert atmosphere. 2-bromopyridine (16.0 g 0.101 moles) was then added over 3 hours whilst the temperature was controlled at between 25 and 30° C. Stirring of the reaction mixture was continued at 25° C. for 3 hours.

Coupling Reaction

Example 5

Preparation of 4-(3'-pyridyl)benzaldehyde 4-bromobenzaldehyde dimethyl acetal (9.5 g, 41.1 mmoles) and palladium tetrakistriphenyl phosphine (50 mg, 0.04 mmoles) were added to a mixture of anhydrous zinc chloride (2.1 g 15.4 mmoles) in anhydrous tetrahydrofuran (23 g), with stirring, in an inert atmosphere. A solution of Grignard A (40.3 g) was added over 4 hours to the resulting mixture, which was kept at 50° C. with stirring, in an inert atmosphere.

The reaction mixture was kept at 50° C. for 30 minutes and then cooled to 20-25° C. An 85% yield of 4-(3'-pyridyl)-benzaldehyde-dimethyl acetal, relative to the 4-bromobenzaldehyde dimethyl acetal loaded, was obtained. After acid hydrolysis, an 85% yield of 4(3'-pyridyl)-benzaldehyde was obtained.

Example 6

Preparation of 4-(3'-pyridyl)benzaldehyde

Example 1 was repeated with the use of a different quantity of anhydrous zinc chloride (7.1 g, 52.1 mmoles), producing a 70% yield of 4-(3'-pyridyl)-benzaldehyde-dimethyl acetal, relative to the 4-bromobenzaldehyde dimethyl acetal loaded.

Example 7

Preparation of 4-(2'-pyridyl)benzaldehyde 4-bromobenzaldehyde dimethyl acetal (9.5 g, 41.1 mmoles) and palladium tetrakistriphenyl phosphine (0.1 g, 0.087 mmoles) were added to a mixture of anhydrous zinc chloride (2.1 g, 15.4 mmoles) in tetrahydrofuran (23 g), with stirring in an inert atmosphere. A solution of Grignard C (41.9 g) was added over 6 hours to the resulting mixture, which was kept at 50° C. with stirring, in an inert atmosphere. The reaction mixture was kept at 50° C. for 30 minutes and then cooled to 20-25° C. A 64% yield of 4-(2'-pyridyl)-benzaldehyde-dimethyl acetal, relative to the 4-bromobenzaldehyde dimethyl acetal loaded, was obtained.

The invention claimed is:
1. A method for the preparation of compound of formula 1,

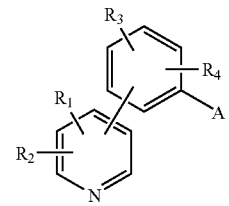

in which a solution containing a compound of formula 2 is added dropwise to a solution containing a compound of formula 3

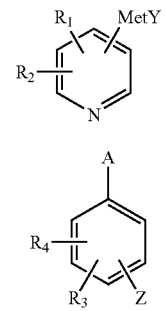

in which:
Met represents Mg or Zn,
Y represents Cl, Br, I or acetoxy,
Z represents I, Br, Cl, triflate, sulphonate, phosphate,
$R_1$, $R_2$, $R_3$, $R_4$, which are the same as one another or different, represent hydrogen, a linear and/or branched $C_1$-$C_4$ alkyl, and/or an aryl, and/or a heteroaryl, or $R_1$ and $R_2$ and/or $R_3$ and $R_4$, taken together, form a $C_3$-$C_8$ ring, an aryl and/or a heteroaryl,
A represents —$COR_5$, where $R_5$ represents hydrogen, a linear and/or branched $C_1$-$C_4$ alkyl, and/or an aryl, and/or a heteroaryl, or
A represents —$CR_5(OR_6)(OR_7)$ where $R_5$ has the meaning described above and $R_6$ and $R_7$, which are the same as one another or different, represent a linear and/or branched $C_1$-$C_4$ alkyl, and/or an aryl, and/or a heteroaryl, or $R_6$ and $R_7$, joined together, represent a $C_1$-$C_8$ alkyl or alkenyl, in the presence of catalytic systems based on palladium or nickel.

2. A method according to claim 1, wherein compound 2 is prepared by reaction of the corresponding halogeno-pyridine with a catalytic quantity of alkyl halide, in the presence of an at least stoichiometric quantity of magnesium.

3. A method according to claim 2, wherein 100 moles of the halogeno-pyridine are reacted with 10-20 moles of alkyl halide and 100-120 moles of magnesium.

4. A method according to claim 2, wherein the alkyl halide is a $C_1$-$C_8$ alkyl chloride or bromide.

5. A method according to claim 4, wherein the alkyl halide is ethyl bromide or isopropyl bromide or chloride.

6. A method according to claim 1, wherein compound 2 is prepared by reaction of the corresponding halogeno-pyridine with an at least stoichiometric quantity of an alkyl-magnesium halide.

7. A method according to claim 6, wherein the alkyl-magnesium halide is a chloride or a bromide of a $C_1$-$C_8$ alkyl-magnesium salt.

8. A method according to claim 1, wherein the palladium and/or the nickel are used in quantities of 0.01-10 moles per 100 moles of compound 2.

9. A method according to claim 1, wherein the solvent is an ethereal solvent, 1,2 dimethoxyethane, and/or 1,1-diethoxymethane, or a THF/toluene mixture.

10. A method according to claim 1, wherein it is performed at a temperature of between 20 and 100° C.

11. A method according to claim 1, wherein it is performed in the presence of phosphines and/or phosphites.

12. A method according to claim 11, wherein the phosphines and/or phosphites are used in a molar ratio of metal: phosphine/phosphite of between 1:1 and 1:6.

13. A method according to claim 11, wherein the phosphines are selected from triaryl phosphines, diarylalkyl phosphines, trialkyl phosphines, and bidentate phosphines.

14. A method according to claim 11, wherein palladium is used in the form of complexes with phosphines.

15. A method according to claim 11, wherein palladium is used in the salt form in combination with a phosphine.

16. A method according to claim 11, wherein nickel is used in the form of complexes with phosphines.

17. A method according to claim 1, wherein it is performed in the presence of zinc salts.

18. A method according to claim 17, wherein the zinc salt is used in quantities of 25-120 moles per 100 moles of compound 2.

19. A method according to claim 18 in which Met is magnesium, wherein 0.01-0.1 moles of palladium and 40-70 moles of zinc are used per 100 moles of compound 2.

20. A method according to claim 17, wherein the molar ratio between palladium and compound 2 is less than 1:100.

21. A method according to claim 1, wherein compound 2 is used in a dynamic deficiency relative to the zinc salt.

22. A method according to claim 1, wherein 0.5-1.2 moles of compound 2 is used per 1 mole of compound 3.

23. A method according to claim 7, wherein the chloride or bromide of a $C_1$-$C_8$ alkyl-magnesium salt is an ethyl or isopropyl magnesium salt.

24. A method according to claim 8, wherein the palladium and/or the nickel are used in quantities of 0.05-2 moles per 100 moles of compound 2.

25. A method according to claim 9, wherein the ethereal solvent is THF.

26. A method according to claim 10, wherein it is performed at a temperature of between 40 and 80° C.

27. A method according to claim 14, wherein the phosphine is $Pd(PPh_3)_4$.

28. A method according to claim 15, wherein the palladium salt is palladium acetate or palladium chloride.

29. A method according to claim 15, wherein the phosphine is triphenyl phosphine.

30. A method according to claim 16, wherein the phosphines are bidentate phosphines.

31. A method according to claim 17, wherein it is performed in the presence of $ZnCl_2$, $ZnBr_2$ or $Zn(OAc)_2$.

32. A method according to claim 18, wherein the zinc salt is used in quantities of 35-70 moles per 100 moles of compound 2.

33. A method according to claim 22, wherein 1 mole of compound 2 is used per 1 mole of compound 3.

\* \* \* \* \*